Figure 1:
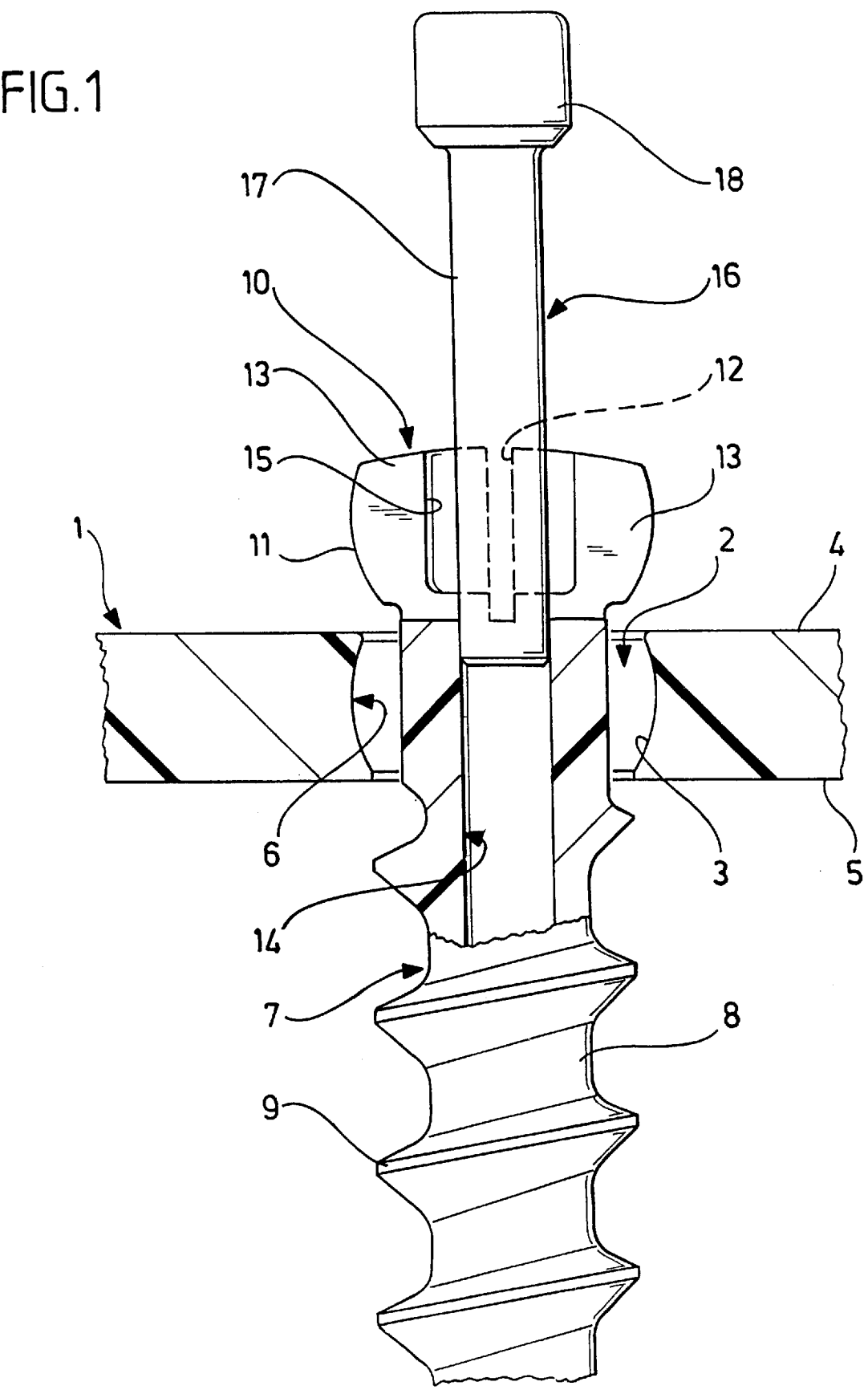

United States Patent
Taddia et al.

[11] Patent Number: 6,117,173
[45] Date of Patent: Sep. 12, 2000

[54] ORTHOPAEDIC FIXING SYSTEM

[75] Inventors: Lino Taddia, Wurmlingen; Rudolf Zepf, Rietheim-Weilheim, both of Germany

[73] Assignee: Aesculap AG & Co., KG, Tuttlingen, Germany

[21] Appl. No.: 09/098,921

[22] Filed: May 29, 1998

Related U.S. Application Data

[63] Continuation of application No. PCT/EP96/05355, Dec. 3, 1996.

[30] Foreign Application Priority Data

Dec. 7, 1995 [DE] Germany .......................... 195 45 612

[51] Int. Cl.[7] ......................................................... A61F 2/28
[52] U.S. Cl. .......................... 623/16.11; 606/72; 606/73; 606/104; 623/17.11
[58] Field of Search .......................... 623/16, 17; 606/71, 606/72, 73, 104

[56] References Cited

U.S. PATENT DOCUMENTS

| | | |
|---|---|---|
| 4,388,921 | 6/1983 | Sutter et al. . |
| 4,484,570 | 11/1984 | Sutter et al. .............................. 606/71 |
| 5,456,719 | 10/1995 | Keller .......................................... 606/71 |
| 5,578,034 | 11/1996 | Estes ........................................... 606/73 |
| 5,735,853 | 4/1998 | Olerud ....................................... 606/71 |

FOREIGN PATENT DOCUMENTS

| | | |
|---|---|---|
| 30 27 148 | 12/1981 | Germany . |
| WO 88/03781 | 6/1988 | WIPO . |
| WO 94/26193 | 11/1994 | WIPO . |

*Primary Examiner*—Michael J. Milano
*Assistant Examiner*—Choon P. Koh
*Attorney, Agent, or Firm*—Barry R. Lipsitz; Douglas M. McAllister

[57] ABSTRACT

In an orthopaedic fixing system comprising at least one implant part which has at least one through-opening, and comprising fixing elements which are inserted into the through-openings, the through-openings having widened portions which receive a head-shaped thickening of the fixing elements, in order to fix the fixing elements in the implant part in an axial direction without however impairing their ability to rotate, it is proposed that the head-shaped thickenings of the fixing elements are compressible, that the widened portions have an outside diameter which is slightly smaller than the non-resiliently-compressed head-shaped thickening, and that the widened portions have undercuts, into which the head-shaped thickening after insertion into the widened portion engages resiliently.

12 Claims, 2 Drawing Sheets

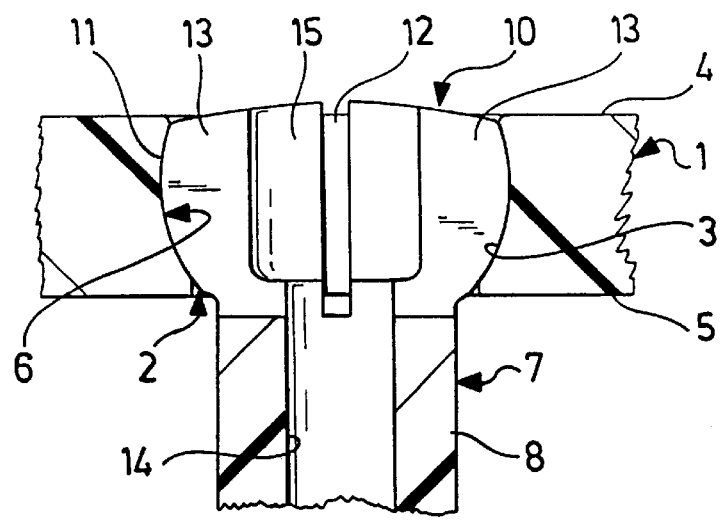
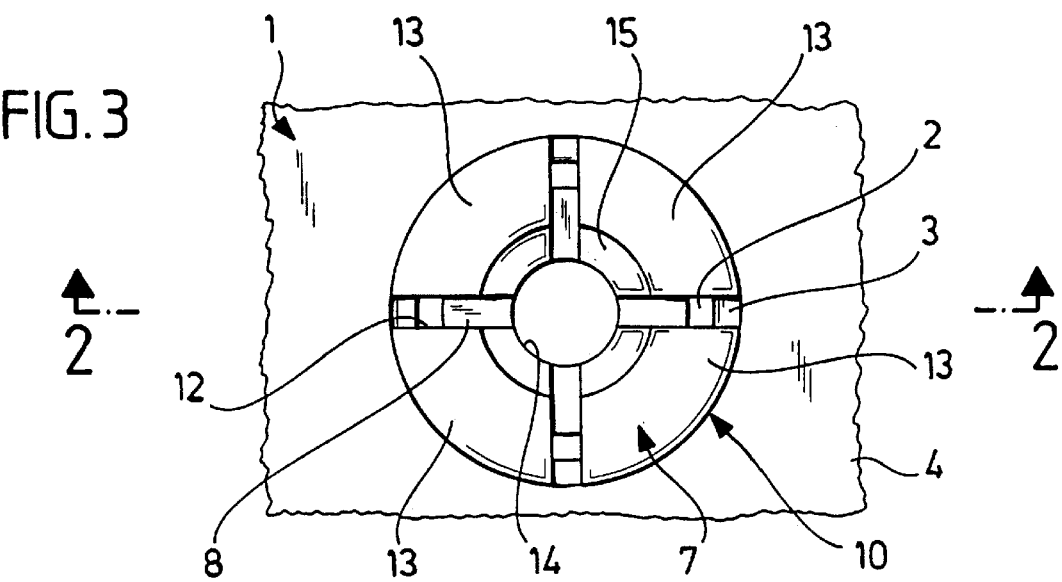
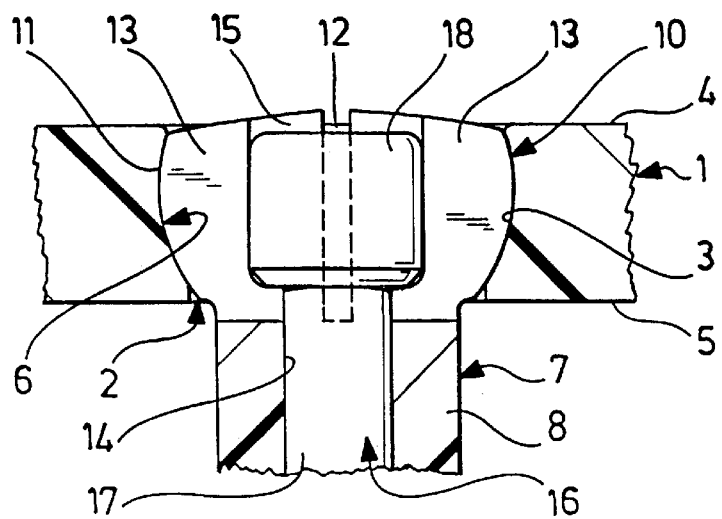

ORTHOPAEDIC FIXING SYSTEM

This application is a continuation of Ser. No. PCT/EP96/05355 filed Dec. 3, 1996.

The invention relates to an orthopaedic fixing system comprising at least one implant part which has at least one through-opening, and comprising pin-shaped fixing elements which are inserted into the through-openings, the through-openings having widened portions which receive a resiliently compressible head-shaped thickening of the fixing elements, the widened portions having an outside diameter which is slightly smaller than the non-resiliently-compressed head-shaped thickening, and the widened portions having undercuts, into which the head-shaped thickening after having been inserted into the widened portion engages resiliently, and comprising a blind hole in the region of the head-shaped thickening of the fixing element, into which blind hole a core is insertable so as to fill it.

Such fixing systems are used to join bone fragments and to fix skeletal parts. The fixing systems may be, for example, bone plates which are fastened by means of bone-screws into the bony substance and therefore pressed against the surface of the bone and fixed there. The systems may also comprise a plurality of implant parts which have to be interconnected, e.g. various bone plates or bone plates, on the one hand, and endo-prostheses, on the other hand.

WO88/03781 describes an osteosynthetic device, wherein a bone-screw may be resiliently latched into a bone plate. To said end, the bone plate has an opening with undercuts, and the head of the bone-screw is resiliently compressible so that it may be snapped resiliently into said undercut opening. In said previously known construction, the bone-screw after having been screwed into the bone is expanded by insertion of a locking pin in such a way that the bone-screw is fixed with a clamping fit in the through-opening of the bone plate, i.e. after insertion of the locking pin, the bone-screw together with the bone plate forms a rigid unit.

The object of the invention is to design an orthopaedic fixing system of the type described in such a way that a bone-screw may be fixed in a captive manner in the undercut through-opening of the plate, while still retaining its ability to rotate freely relative to the plate.

In an orthopaedic fixing system of the type described initially, said object is achieved according to the invention in that the core is so dimensioned that, in its position after insertion into the blind hole, it locks the head-shaped thickening without expanding said head-shaped thickening.

Said insertable core, which does not push apart the parts of the head-shaped thickening but merely fills the blind hole without expanding said blind hole, prevents the resiliently bendable parts of the head-shaped thickening from being resiliently bendable in a radially inward direction, so that merely the insertion of said core locks the head-shaped thickening in the widened portion of the through-opening when the head-shaped thickening engages into the undercut of the widened portion. Since the head-shaped thickening is not expanded by said core, the head-shaped thickening remains freely rotatable in the widened portion, with locking being effected solely by the form closure in an axial direction.

Said ability of the thickening to rotate freely in the widened portion means that, given combination systems, the implant parts obtain a specific mobility relative to the bone system, although the fixing elements are firmly anchored in the bone or on other implant parts. Thus, in the event of changes e.g. as a result of osteolysis or bone resorption, the implant parts or the fixing elements are prevented from being able to break as a result of an undesired action of force.

In principle, the implant parts may take a wide variety of forms. For example, they may be bone plates, which are fixed by being screwed on the bone with the aid of a fixing element in the form of a bone-screw and hence fix bone fragments. It is also possible for a plurality of implant parts to be joined directly to one another by means of a fixing element, e.g. two bone plates or a bone plate, on the one hand, and the shaft of an endo-prosthesis, on the other hand.

Furthermore, it goes without saying that the term "bone plate" covers not only purely plate-like components but also differently shaped implants which are used to fix and support the bone system. Similarly, the term "bone-screw" embraces not only, in the true sense, fixing pins screwable into bony substance but also, in general, pin-shaped fixing elements with a head-shaped thickening which penetrate the bone plates. The latter may also be fixed by means of a screw-on nut or other tightening means on the bone system, it not being absolutely necessary for them to be anchored by their own threads in the bony substance itself.

In a preferred embodiment of the invention, it may be provided that the head-shaped thickening is formed by a plurality of parts of the fixing element, which are capable of bending resiliently in a radially inward direction.

In said case, it is advantageous when the resiliently inwardly bendable parts are portions of the fixing element, which are formed integrally with the fixing element and separated from one another by radially extending recesses. To realize the required compressibility, it is therefore in principle already sufficient for a fixing element made of resilient material to have in the region of the head-shaped thickening one or more radially extending recesses, which enable the parts of the fixing element to move slightly closer together.

It may be provided that the blind hole narrows in steps or stages towards the free end of the fixing element. In said case, the blind hole may extend as far as into the shaft of the fixing element, the core then carrying a suitable lengthening pin, which substantially completely fills the blind hole.

It is advantageous when the blind hole is circular cylindrical in shape.

In a particularly preferred embodiment, it is provided that the widened portion has an inner surface shaped as an annular section of a sphere and the head-shaped thickening has a complementary outer surface shaped as an annular section of a sphere, of which the maximum diameter is disposed in the interior of the implant part at a distance from the latter's outer surface.

Such a refinement makes it possible to swivel the fixing element through a specific angular range in the widened portion of the through-opening to allow it to be screwed in obliquely relative to the implant part. Nevertheless, the fixing element remains fixed in the implant part. The same applies also when a core has been inserted into a blind hole and locks the fixing element against removal from the implant part. An ability of the fixing element to rotate freely about the longitudinal axis and about axes of rotation lying in the plane of the implant part is however, in said case, fully retained.

In a particularly preferred embodiment, it is provided that the fixing element is a bone-screw.

In a modified embodiment, the fixing element may be a screw with a cut thread or tap. While the bone-screw is suitable for screwing into bony substance, a fixing element with a cut thread may be used to join two implant parts to one another. It is then advantageous when one implant part has an internal thread, into which the fixing element may be screwed, while the other implant part in the described manner has a through-opening with an undercut widened portion for the head of the fixing element. Two bone plates, for example, may be joined to one another in said manner. It is also possible, in the case of a long bone, for the shaft of an endo-prosthesis introduced into said bone to be connected to a bone plate lying against the outside of the bone, the fixing element then passing through the wall of the bone.

A more detailed explanation is provided by the following description of a preferred embodiment of the invention in connection with the drawings. The drawings show:

FIG. 1: a part-sectional side view of a bone plate and of a bone-screw plus core inserted in a through-opening of the bone plate, prior to pressing of the bone-screw into the through-opening;

FIG. 2: a view similar to FIG. 1 of the bone-screw of FIG. 1, which is pressed into the bone plate but not locked in axial direction, in the region of the bone plate and the head-shaped thickening in a section along line 2—2 in FIG. 3;

FIG. 3: a plan view of the bone plate and the inserted bone-screw of FIG. 2 and

FIG. 4: a view similar to FIG. 2 with an inserted core for locking the bone-screw in axial direction.

There now follows a description of the orthopaedic fixing system using the example of a bone plate, which is to be fastened with the aid of bone-screws to bony substance. It goes without saying, however, that the invention is not restricted to the use on bone plates and the employment of bone-screws but is generally directed towards orthopaedic fixing systems, in which implant parts are to be fastened to the bone system or to one another with the aid of fixing elements.

The orthopaedic fixing system illustrated in the drawings comprises a metal bone plate 1 having a plurality of through-openings 2, of which only one is shown in the drawings. Said through-opening has an inner wall 3 shaped as an annular section of a sphere, the region of maximum diameter of the through-opening 2 being disposed substantially in the middle of the bone plate 1 with the result that the through-opening 2 narrows both towards the top surface 4 and towards the underside 5. The inner wall 3 shaped as an annular section of a sphere therefore forms a bulging and hence an undercut 6.

Inserted into the through-opening 2 is a bone-screw 7 which may, for example, be made of a resilient plastics material, in particular of resorbtive plastics material.

Said bone-screw 7 comprises a shaft 8 with an external thread 9 as well as a head-shaped thickening 10, which is laterally delimited by a surface 11 shaped as an annular section of a sphere, the dimensions of which correspond substantially to the dimensions of the inner wall 3 of the through-opening 2 likewise shaped as an annular section of a sphere. The peripheral surface 11 is therefore designed to be complementary to the inner wall 3.

Two diametrical recesses 12, which are disposed at right angles to one another and extended from above through the entire height of the head-shaped thickening 10 into the bone-screw 7, divide the head-shaped thickening 10 into four portions 13 separated from one another in a peripheral direction and therefore produce a specific resiliency of said portions 13, i.e. the portions 13 are capable of being bent resiliently in a radially inward direction.

Worked into the bone-screw 7 is a central blind hole 14, which extends as far as into the shaft 8 and has, in the region of the head-shaped thickening 10, a widened region 15. Said widened region 15 facilitates the resilient compression of the head-shaped thickening 10, of which the portions 13 are bent resiliently inwards. By virtue of said compressing of the head-shaped thickening 10, its outside diameter may be reduced so that the head-shaped thickening 10 may be pushed into the through-opening 2 even though the latter at the narrower transition points with the top surface 4 and the underside 5 has an inside diameter which is smaller than the outside diameter of the non-deformed, non-compressed head-shaped thickening 10. Said head-shaped thickening 10 in the course of insertion is resiliently compressed and after insertion springs apart again, the convex peripheral surface 11 engaging into the undercut 6 of the through-opening 2. As a result, the bone-screw 7 is fixed in axial direction in the through-opening 2 without, however, impairing the ability of the bone-screw to rotate freely about its longitudinal axis and, in addition, about swivelling axes lying in the plane of the bone plate 1. Thus, a pivot-like connection is formed between bone-screw 7 and bone plate 1.

The bone-screw 7 may be turned in a suitable manner by means of a tool which may engage, for example, into the recesses 12 or into the blind hole 14, which may have for said purpose a non-circular cross section, e.g. a hexagonal cross section.

A core 16 is insertable into the blind hole 14 and is shaped in such a way that it substantially completely fills the blind hole 14. The core 16 comprises an elongate pin 17, which engages into the bottom part of the blind hole 14 disposed in the shaft 8, and a cylindrical thickening 18, which engages into the widened region 15 of the blind hole 14. The dimensions selected are such that the core 16 passes into the blind hole 14 without expanding the blind hole.

Once the core 16 has been inserted in said manner into the bone-screw 7, the fact that the widened region 15 of the blind hole 14 is completely filled prevents the resilient bending of the portions 13 in a radially inward direction, i.e. it is no longer possible to reduce the outside diameter of the head-shaped thickening 10 of the bone-screw 7. Once the bone-screw 7 has been inserted into the through-opening 2, it is therefore no longer possible to remove the head-shaped thickening 10 from the undercut 6, the resultant effect being that the bone-screw 7 is locked, without however being jammed, in the bone plate 1. Despite said locking, the bone-screw remains held in a freely rotatable and freely pivotal manner in the through-opening 2, with the result that the pivot-like quality of the connection between bone-screw 7 and bone plate 1 is in no way impaired.

What is claimed is:

1. An orthopaedic fixing system comprising:
   at least one implant part which has at least one through-opening,
   at least one pin-shaped fixing element having a head comprising a widened portion in the form of a head-shaped thickening which is resiliently compressible for insertion into a corresponding through-opening, the through-opening having a widened portion which receives the resiliently compressible head-shaped thickening of the fixing element, the widened portion of the through-opening having an outside diameter which is slightly smaller than the head-shaped thickening when the head-shaped thickening is in a non-compressed state, and the widened portion of the through-opening having undercuts, into which the head-shaped thickening engages resiliently after insertion into the widened portion,
   a blind hole extending into the head-shaped thickening of the fixing element, and a core which is insertable so as to fill the blind hole wherein the core is so dimensioned that, in its position after insertion into the blind hole, it locks the head-shaped thickening without expanding said head-shaped thickening.

2. A fixing system according to claim 1, wherein the head-shaped thickening is formed by a plurality of parts of the fixing element, which are resiliently bendable in a radially inward direction.

3. A fixing system according to claim 2, wherein the resiliently inwardly bendable parts are portions of the fixing element, which are formed integrally with the fixing element and separated from one another by radially extending recesses.

4. A fixing system according to claim 1, wherein the blind hole narrows in stages towards a free end of the fixing element.

5. A fixing system according to claim 1, wherein the blind hole is circular cylindrical in shape.

6. A fixing system according to claim 1, wherein the widened portion of the through-opening has an inner surface shaped as an annular section of a sphere and the head-shaped thickening has a complementary outer surface shaped as an annular section of a sphere, the maximum diameter of which is disposed in the interior of the implant part at a distance from the outer surfaces of the implant part.

7. A fixing system according to claim 1, wherein the fixing element is a bone-screw.

8. A fixing system according to claim 1, wherein the fixing element is a screw with a cut thread.

9. A fixing system according to claim 1, wherein the implant part is a bone plate.

10. A fixing system according to claim 1, wherein the fixing element connects two or more implant parts to one another.

11. A fixing system according to claim 10, wherein the implant parts are plate-shaped.

12. A fixing system according to claim 10, wherein one implant part is a bone plate and another implant part is an endo-prosthesis.

* * * * *